(12) United States Patent
Benkert et al.

(10) Patent No.: US 12,254,593 B2
(45) Date of Patent: Mar. 18, 2025

(54) METHODS AND SYSTEMS FOR GENERATING COMBINED IMAGE DATA BASED ON MR DATA

(71) Applicant: Siemens Healthcare GmbH, Erlangen (DE)

(72) Inventors: Thomas Benkert, Neunkirchen am Brand (DE); Marcel Dominik Nickel, Herzogenaurach (DE)

(73) Assignee: Siemens Healthineers AG, Erlangen (DE)

( * ) Notice: Subject to any disclaimer, the term of this patent is extended or adjusted under 35 U.S.C. 154(b) by 356 days.

(21) Appl. No.: 17/465,215

(22) Filed: Sep. 2, 2021

(65) Prior Publication Data

US 2022/0067896 A1    Mar. 3, 2022

(30) Foreign Application Priority Data

Sep. 3, 2020    (DE) .......................... 102020211107.3

(51) Int. Cl.
*G06T 5/50*    (2006.01)
*A61B 5/055*    (2006.01)
(Continued)

(52) U.S. Cl.
CPC ................ *G06T 5/50* (2013.01); *A61B 5/055* (2013.01); *G01R 33/5608* (2013.01);
(Continued)

(58) Field of Classification Search
None
See application file for complete search history.

(56) References Cited

U.S. PATENT DOCUMENTS 6,169,817 B1 *  1/2001  Parker .................... G06T 7/215
                                                345/419
9,651,640 B2 *  5/2017  Feiweier .............. G01R 33/565
                        (Continued)

OTHER PUBLICATIONS

Brown, Mark A. and Semelka, Richard C., MRI Basic Principles and Applications, 2003, John Wiley & Sons, Inc., Third Edition, p. 68-71 (Year: 2003).*

(Continued)

*Primary Examiner* — Siamak Harandi
*Assistant Examiner* — Caroline Tabancay Duffy
(74) *Attorney, Agent, or Firm* — Banner & Witcoff Ltd.

(57) ABSTRACT

In a method for generating combined image data based on first magnetic resonance (MR) data and second MR data, the first MR data and the second MR data are provided, the first MR data having been generated by a first actuation of a magnetic resonance device from an examination area of an examination object using a first sequence module, and the second MR data having been generated by a second actuation of the magnetic resonance device from the examination area of the examination object using the first sequence module, the first MR data and the second MR data are registered to one another to generate first registered MR data and second registered MR data; the first registered MR data and the second registered MR data are statistically combined to generate combined image data, and the combined image data is provided as an output in electronic form as a data file.

22 Claims, 4 Drawing Sheets

(51) Int. Cl.
*G01R 33/56* (2006.01)
*G01R 33/561* (2006.01)
*G06T 3/153* (2024.01)
*G06T 7/11* (2017.01)
*G06T 7/33* (2017.01)

(52) U.S. Cl.
CPC .......... *G01R 33/5617* (2013.01); *G06T 3/153* (2024.01); *G06T 7/11* (2017.01); *G06T 7/33* (2017.01); *G06T 2207/10088* (2013.01); *G06T 2207/20081* (2013.01); *G06T 2207/20216* (2013.01); *G06T 2207/30008* (2013.01); *G06T 2207/30081* (2013.01); *G06T 2207/30168* (2013.01)

(56) References Cited

U.S. PATENT DOCUMENTS

| | | | |
|---|---|---|---|
| 2012/0051664 A1* | 3/2012 | Gopalakrishnan | G06T 5/40 382/294 |
| 2012/0074940 A1* | 3/2012 | Kimura | G01R 33/561 324/318 |
| 2014/0091798 A1* | 4/2014 | Arunachalam | G01R 33/54 324/309 |
| 2016/0077180 A1* | 3/2016 | Beck | G01R 33/56509 324/309 |
| 2016/0349343 A1* | 12/2016 | Zeller | G01R 33/56554 |
| 2018/0089863 A1* | 3/2018 | Marschner | G01R 33/56545 |
| 2019/0011518 A1* | 1/2019 | Feiweier | G01R 33/36 |
| 2020/0211209 A1* | 7/2020 | Liao | G06T 7/30 |
| 2021/0390696 A1* | 12/2021 | Iwase | G06T 5/60 |

OTHER PUBLICATIONS

Brown, Mark A. and Semelka, Richard C., MRI Basic Principles and Applications, 2003, John Wiley & Sons, Inc., Third Edition, p. 68-71 (Year: 2003) (Year: 2003).*

Brown, Mark A. and Semelka, Richard C., MRI Basic Principles and Applications, 2003, John Wiley & Sons, Inc., Third Edition, p. 68-71 (Year: 2003) (Year: 2003) (Year: 2003).*

Clare, Stuart. Functional MRI: Methods and Applications. University of Nottingham, Oct. 1997. (Year: 1997).*

Clare, Stuart. Functional MRI: Methods and Applications. University of Nottingham, Oct. 1997. (Year: 1997) (Year: 1997).*

Eklund, Anders. Signal Processing for Robust and Real-Time fMRI with Application to Brain Computer Interfaces, Linkopings Universitet (Sweden), Sweden, 2010. ProQuest, https://www.proquest.com/dissertations-theses/signal-processing-robust-real-time-fmri-with/docview/3091533058/se-2. (Year: 2010).*

Gracien et al., "Evaluation of brain ageing: a quantitative longitudinal MRI study over 7 years," Eur Radiol., vol. 27, pp. 1568-1576 (2017).

Padhani et al., "Evaluating the Effect of Rectal Distention and Rectal Movement on Prostate Gland Position Using Cine MRI," Int. J. Radiation Oncology Biol. Phys., vol. 44, No. 3, pp. 525-533 (1999).

Mok et al., "Fast Symmetrie Diffeomorphic Image Registration with Convolutional Neural Networks," Proceedings of the IEEE/CVF Conference on Computer Vision and Pattern Recognition (CVPR), pp. 4644-4653 (2020).

German Office Action for Application No. 102020211107.3 dated May 21, 2021.

* cited by examiner

METHODS AND SYSTEMS FOR GENERATING COMBINED IMAGE DATA BASED ON MR DATA

CROSS REFERENCE TO RELATED APPLICATIONS

This patent application claims priority to German Patent Application No. 10 2020 211 107.3, filed Sep. 3, 2020, which is incorporated herein by reference in its entirety.

BACKGROUND

Field

The disclosure relates to a method, an image processing system, a magnetic resonance (MR) device, a computer program product and an electronically readable data carrier for generating combined image data based on first and second MR data generated with the same sequence module.

Related Art

In a magnetic resonance device, the body to be examined of an examination object, in particular a patient, is usually exposed with the aid of a main magnet to a relatively high main magnetic field, for example 1.5 or 3 or 7 tesla. In addition, gradient pulses are emitted with the aid of a gradient pulse unit. High-frequency radio-frequency pulses, for example excitation pulses are then emitted via a radio-frequency antenna unit by means of suitable antenna facilities, which leads to the nuclear spins of specific atoms excited resonantly by these radio-frequency pulses being flipped by a defined flip angle in relation to the magnetic field lines of the main magnetic field. Upon the relaxation of the nuclear spins, radio-frequency signals, so-called magnetic resonance signals, are emitted, received by means of suitable radio-frequency antennas and then further processed. Finally, the desired image data can be reconstructed from the raw data acquired in this way.

Therefore, for a specific scan, it is necessary to transmit a specific magnetic resonance control sequence (MR control sequence), also called a pulse sequence, consisting of a sequence of radio-frequency pulses, for example excitation pulses and refocusing pulses, and gradient pulses that are to be transmitted suitably coordinated therewith in different gradient axes along different spatial directions. Timed to coincide with this, readout windows are set which specify the time periods in which the induced magnetic resonance signals are acquired. The MR control sequence is embodied in such a way that the image data to be reconstructed from the magnetic resonance signals map, in particular depict, a diagnostic area, i.e., a spatial section of the examination object. The diagnostic area typically comprises a large number of spatially resolved voxels. The diagnostic area can be embodied as a three-dimensional shape, in particular as a cuboid. The diagnostic area typically comprises a plurality of slices arranged in parallel. A slice can be defined in that in each case it only has one voxel perpendicular to the plane defined by the parallel arrangement. The diagnostic area can also comprise a plurality of slabs arranged in parallel. A slab can be defined in that it in each case has a defined number of voxels perpendicular to the plane defined by the parallel arrangement, said defined number of voxels being at most 80%, preferably at most 65%, particularly preferably at most 50% of the number of voxels in a direction perpendicular thereto.

An MR control sequence comprises a plurality of sequence modules. A sequence module is typically a temporal section of an MR control sequence comprising at least one radio-frequency pulse and/or one gradient pulse and/or one readout window. A temporal sequence of the radio-frequency pulses and/or gradient pulses and/or readout windows comprised by a sequence module is typically prespecified for the generation of image data with a specific contrast and/or defined by the nature of the MR control sequence. For example, an MR control sequence embodied as a gradient echo sequence can use a gradient pulse for refocusing. An MR control sequence embodied as a spin-echo sequence, in particular as HASTE or TSE, can use at least one radio-frequency pulse for refocusing.

In an exemplary embodiment, a sequence module is a self-contained section of an MR control sequence, according to which section MR data from a defined examination area of the examination object is generated and/or recorded. The MR data recorded as part of a sequence module can comprise magnetic resonance signals and/or raw data and/or image data reconstructed from such raw data. An examination area can correspond to the diagnostic area. An examination area can comprise a sub-area of the diagnostic area. An examination area can comprise one slice and/or at least two slices of the diagnostic area. An examination area is in particular a spatial section of the examination object.

To improve the signal-to-noise ratio, depending upon the diagnostic area and the MR control sequence used, an examination area can be acquired twice or multiple times by means of the same sequence module so that accordingly MR data from the same examination area with the same recording technique is present on a multiple basis and combined to generate the final image data; i.e., combined image data is generated. However, this method is sensitive with regard to movement of the examination object. A movement of the examination object can generate a change, in particular a displacement and/or distortion of the examination area, said change not being identified during the recording of the MR data. As a result, movement of the examination object may result in the final image data being blurred and detailed structures being no longer visible.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

The disclosure is based on the object of disclosing a method for generating combined image data based on first and second MR data, in each case generated with the same sequence module from the same examination area, which compensates motion artifacts in a particularly robust and precise manner.

The method according to the disclosure for generating combined image data based on first MR data, said first MR data having been generated by a first actuation of a magnetic resonance device from an examination area of an examination object using a first sequence module, and based on second MR data, said second MR data having been generated by a second actuation of the magnetic resonance device from the examination area of the examination object using the first sequence module, provides the following method steps:
  providing the first MR data and the second MR data,
  generating first registered MR data and second registered MR data by registering the first MR data and the second MR data to one another,
  generating combined image data by statistical combination of the first registered MR data and the second registered MR data,
  providing the combined image data.

In an exemplary embodiment, the first MR data and second MR data only differ in the point in time at which they were generated from the same examination area of the same examination object using the same first sequence module. In an exemplary embodiment, the first MR data and second MR data were generated as part of an MR control sequence, in particular as part of the actuation of a magnetic resonance device according to an MR control sequence. In an exemplary embodiment, the first actuation and the second actuation are based on the assumption that the examination area has the same position and/or shape and/or spatial extent and/or is unchanged during the first actuation and the second actuation. In an exemplary embodiment, a MR control sequence comprising the first sequence module is free of a navigator and/or motion detection. The first actuation and the second actuation preferably differ purely in terms of time. A contrast agent may have been administered to the examination object between the first actuation and the second actuation. The first MR data and second MR data can be present in the form of stored data to which the method according to the disclosure has access during said provision.

If the first MR data and the second MR data comprise image data, the registration is embodied as an image registration of the first MR data to the second MR data. If the first MR data comprises raw data and the second MR data comprises raw data, registration can take place in the raw data space. If the first MR data comprises raw data and the second MR data comprises raw data, first registered MR data and the second registered MR data can in each case be registered raw data. In this case, the generation of the combined image data can comprise reconstruction of the first registered MR data and the second registered MR data. In an exemplary embodiment, the registration of the first MR data and the second MR data comprises the adjustment of differences, in particular differences in the depiction, of the examination area in the first MR data and the second MR data.

The statistical combination of the first registered MR data and the second registered MR data can take place voxel-by-voxel. The statistical combination of the first registered MR data and the second registered MR data can comprise a formation of a combined data value for each data point of the first registered MR data and each data point of the second registered MR data. In an exemplary embodiment, the combined image data comprises a value for each voxel of the examination area.

It is conceivable that, in addition to the first MR data and the second MR data, further MR data, generated by at least one further actuation of the magnetic resonance device from the examination area of the examination object using the first sequence module, is provided to the method, this further MR data is registered similarly to the first and second MR data and the further registered MR data is taken into account in the statistical combination and generation of the combined image data.

The advantage of the method according to the disclosure consists in the fact that any changes to the examination area that occur between the first actuation and the second actuation, for example due to movement of the examination object, can in particular be particularly effectively corrected and/or reduced by the registration. The quality of the combined image data is increased by the method according to the disclosure compared to a conventional combination of repeated scans. In particular, blurring can be reduced and image sharpness increased. The duration of the generation of the combined image data and/or the duration for the acquisition of the first MR data and second MR data, in particular the duration of the MR control sequence comprising the first sequence module, is not increased by the method according to the disclosure since the method according to the disclosure takes place independently of the recording of the first MR data and the second MR data. As a result, execution can also be particularly robust. Consequently, the method according to the disclosure results in higher quality of the combined image data without extending the scan duration. In addition, it is possible to dispense with drugs used for sedation and/or immobilization of the examination object.

The improved image quality resulting from the method according to the disclosure reduces the probability of having to repeat the MR control sequence and/or arranging a new appointment for a new examination with the examination object. Likewise, the risk of misdiagnosis can be reduced.

One embodiment of the method provides that the examination area comprises at least one of the following structures:
- prostate,
- abdomen,
- pelvis,
- chest,
- head,
- joint,
- musculoskeletal unit.

In particular in the case of T2-weighted prostate imaging using a TSE-based (TSE=turbo-spin echo) MR control sequence and/or with T2-weighted abdominal MR imaging using a HASTE-based (HASTE=half-Fourier acquisition single-shot turbo spin-echo) MR control sequence, motion artifacts occur in about 30% of examination objects in combined image data, as described in Padhani A et al, Int. J. Radiation Oncology Biol. Phys., Vol. 44, No. 3, pp. 525-533. Since, in particular movements occur naturally and subconsciously in the abdomen and/or the prostate and/or the pelvis and/or the chest, butylscopolamine and/or glucagon is typically administered to immobilize the bowel in the context of conventional MR imaging. This embodiment enables the administration of the drug to be dispensed with, thus enabling the acquisition of the MR data to take place more quickly, with less risk and in a non-invasive manner.

In musculoskeletal and/or head imaging, a high resolution of the image data is typically required for diagnosis, so typically multiple repetitions are executed in order to improve the signal-to-noise ratio, i.e., an examination area is acquired multiple times by the same sequence module and the data is then combined. This can lead to long scan durations for the associated MR control sequence, as a result of which the probability of the examination object moving during and/or between the first actuation and/or the second actuation is particularly high. Consequently, this embodiment of the method can be particularly effective for this application.

One embodiment of the method provides that the registration comprises a rigid registration. A rigid registration can be executed particularly efficiently and robustly. In particular, if the examination area comprises a head and/or a musculoskeletal unit, movements of the examination area are predominantly rigid, i.e., can be described by translation and rotation and/or no elastic deformations occur.

One embodiment of the method provides that the first MR data comprises first raw data and the second MR data comprises second raw data and the registration takes place taking into account a change in phase between the first raw data and the second raw data.

A rigid change in the examination area, for example in musculoskeletal and/or head imaging, results in a change, in particular a local change, of phase in the raw data space. The registration of the first MR data and the second MR data can identify and compensate the change in phase, in particular locally. Consequently, this embodiment is particularly suitable for rigid registration and/or for compensating rigid changes to the examination area.

One embodiment of the method provides that the registration comprises an elastic registration, in particular a non-rigid registration. An elastic registration, in particular a non-rigid registration, is particularly suitable for compensating local changes and changes to clinically relevant regions, such as, for example, the prostate.

One embodiment of the method provides that the registration of the first MR data and the second MR data to one another comprises the following method steps:

in each case, segmenting a structure comprised by the examination area and/or identifying a landmark comprised by the examination area in the first MR data and the second MR data, registering the structure and/or the landmark of the first MR data and the second MR data to one another.

In an exemplary embodiment, the first MR data and the second MR data are embodied as image data or the registration of the first MR data and the second MR data comprises a reconstruction of the first MR data and the second MR data in each case to form image data. The examination area preferably comprises a structure, which is, for example, an organ and/or a physiological unit and/or a sub-area of an organ. The examination area preferably comprises a landmark, which is, for example, a prominent area of an organ and/or a physiological unit. The first MR data and the second MR data preferably include the structure and/or the landmark. According to this embodiment, the registration of the first MR data and the second MR data to one another takes place taking into account the structure and/or the landmark.

This embodiment enables a particularly precise registration by taking into account in the examination area and/or for creating a diagnosis for relevant sub-areas and/or landmarks of the examination area. This type of registration is particularly suitable for reducing or eliminating blurring in the combined image data, in particular also in detailed sub-areas and/or in a clinically relevant region.

One embodiment of the method provides that the first MR data comprises first raw data and the second MR data comprises second raw data, and the registration of the first MR data and the second MR data to one another comprises a reconstruction of the first raw data and the second raw data taking into account a similarity condition.

Accordingly, the reconstruction can be embodied such that, during the reconstruction of the first raw data and the second raw data, in particular during their joint reconstruction, a similarity between the first raw data and the second raw data is identified and/or enforced. In particular, the registration can enforce a similarity during the reconstruction. The registration can then also be free of rigid and/or elastic registration. The similarity condition can comprise a threshold value for a property to be quantified and established in the course of the registration. For example, the similarity condition can comprise a maximum phase difference between the first raw data and the second raw data. The registration can comprise a determination of a phase difference in at least one region in the first raw data and the second raw data. If the maximum phase difference is exceeded, the registration can comprise a phase correction of the first raw data and/or the second raw data and a reconstruction of the correspondingly corrected first raw data and second raw data.

The reconstruction of the first raw data and the second raw data can take place simultaneously and/or at least partially overlapping in time with the registration of the first raw data and the second raw data. In particular, the registration and/or results of the registration can be taken into account during the reconstruction.

The reconstruction can also take place using a compressed sensing method.

In this way, motion artifacts in the combined image data can be reduced particularly effectively, since a similarity can already be ensured between the first raw data and the second raw data.

One embodiment of the method provides that the reconstruction of the first MR data and the second MR data takes place using a trained function. The trained function can comprise a neural network and/or a deep-learning method. It is known that reconstruction algorithms using trained functions, in particular neural networks and/or machine-learned functions and/or deep-learning methods, are particularly suitable for reconstruction, in particular of subsampled raw data. Accordingly, this embodiment enables the use of a first sequence module, which subsamples the raw data space when recording the MR data. Alternatively and/or additionally, this embodiment can enable the generation of higher quality combined image data while the quality of the raw data remains unchanged.

One embodiment of the method provides that the registration of the first MR data and the second MR data to one another takes place using a non-linear algorithm and/or a trained function. The trained function and/or the non-linear algorithm have preferably been trained in advance with a large number of first MR data items and second MR data items from test objects which have been subject to a large number of movements and/or changes in position. This enables changes between the first MR data and the second MR data to be identified particularly efficiently and compensated by registration. Accordingly, this embodiment enables particularly good compensation of motion artifacts.

One embodiment of the method provides that the first registered MR data comprises first image data, having a first intensity value for each voxel comprised by the examination area and the second registered MR data comprises second image data having a second intensity value for each voxel comprised by the examination area, and the statistical combination of the first registered MR data and the second registered MR data comprises averaging the first and second intensity values for each voxel.

Image data is typically defined by spatially resolved intensity values, wherein the intensity values indicate the intensity of the MR signal at the position of the voxel. Let k=1 for the first MR data items and k=2 for the second MR data items of the examination area which is defined by the coordinates (x,y). Overall further MR data items, overall n MR data items recorded for the examination area can be provided with the first sequence module. Let the intensity value for the kth MR data items be defined by $I_k$. If the statistical combination comprises the formation of an average, the combined image data can be determined according to $$I(x, y) = \frac{1}{n} \sum_{k=1}^{n} I_k(x, y).$$

This enables uniform weighting of all the MR data provided, as a result of which the combined image data can be determined in a particularly simple and automated manner.

One embodiment of the method provides that the statistical combination of the first registered MR data and the second registered MR data is subject to weighting, in particular location-dependent weighting, corresponding to a quality of the first registered MR data and the second registered MR data.

The weighting can be provided in the form of a weighting factor $\mu_k(x,y)$. The method can comprise the determination of a weighting factor based on the MR data provided. In an exemplary embodiment, the weighting factor has different values for the first MR data and the second MR data. The combined image data can be determined according to $$I(x, y) = \frac{1}{\sum_{k=1}^{n} \mu_k(x, y)} \sum_{k=1}^{n} \mu_k(x, y) I_k(x, y).$$

In an exemplary embodiment, the weighting factor is greater the higher the quality of the corresponding MR data. If the first MR data have ghost artifacts and/or motion artifacts, the first MR data can be excluded from the combined image data with a weighting factor $\mu_k(x,y)=0$ for k=1 and all x, y. This embodiment enables a particularly robust correction of motion artifacts in the combined image data.

One embodiment of the method provides that the examination object has executed a movement and/or a change in position during the first actuation and/or during the second actuation and/or between the first actuation and the second actuation.

This movement and/or the change in position can have the effect that the first MR data and the second MR data can be different from one another. The resulting difference can particularly advantageously be corrected by the registration. Consequently, this embodiment of the method according to the disclosure benefits particularly well from the integrated motion correction.

One embodiment of the method provides that the first actuation and the second actuation at least partially overlap in time and/or have a time difference of less than 10 minutes, preferably less than 5 minutes, particularly preferably less than 3 minutes. This embodiment provides that the first MR data and second MR data are not recorded at two different time points, for example in a longitudinal study as part of the monitoring of the course of a disease and/or therapy. Rather, the first MR data and the second MR data are preferably recorded as part of an examination, during which examination the examination object is positioned in the magnetic resonance device such that MR data can be acquired continuously. In particular, a pause between the first actuation and the second actuation, during which pause the magnetic resonance device is free of actuation corresponding to a sequence module, lasts 20 seconds, preferably 10 seconds at the most, particularly preferably 5 seconds at the most. Accordingly, this embodiment enables displacement and/or distortion of the examination area due to a movement during an examination of the examination object to be corrected.

One embodiment of the method provides that the first sequence module is part of an MR control sequence, said MR control sequence comprising at least two further sequence modules for generating further MR data from at least two further examination areas of the examination object.

In an exemplary embodiment, the MR control sequence is embodied to acquire MR data from a diagnostic area of the examination object. In an exemplary embodiment, the examination area and the at least two further examination areas are part of the diagnostic area.

In an exemplary embodiment, the MR control sequence provides a first actuation and a second actuation of the magnetic resonance device using a first further sequence module of the at least two further sequence modules for generating MR data from a first further examination area of the at least two further examination areas. In an exemplary embodiment, the MR control sequence provides a first actuation and a second actuation of the magnetic resonance device using a second further sequence module of the at least two further sequence modules for generating MR data from a second further examination area of the at least two further examination areas. The examination area and the at least two further examination areas can, for example, be slices and/or slabs arranged parallel to one another, wherein in each case an examination area comprises a slice and/or a slab.

The registration of the MR data and the generation of combined image data as described in the context of the method according to the disclosure is preferably also applied to the MR data of the at least two further examination areas. This embodiment enables the processing of the entire diagnostic area.

One embodiment of the method provides that is embodied as a spin-echo sequence, in particular as a turbo spin-echo sequence (TSE) and/or as a half-Fourier acquisition single-shot turbo spin-echo sequence (HASTE). In particular an MR control sequence embodied as a spin-echo sequence, TSE and/or HASTE, in particular with T2 weighting, has a particularly long scan duration and/or a particularly low signal-to-noise ratio as a result of which repeated recording of the same examination area with the same parameters, i.e., with the first sequence module, and a subsequent combination of the data to form combined image data is particularly important. In particular, T2-weighted image data is a core element of diagnosis in virtually all clinical MR examinations. Consequently, a combination of the method according to the disclosure with MR data generated by such an MR control sequence is particularly advantageous.

Furthermore, the disclosure is based on an image processing system with an image processor comprising an input, an output, a registration unit and a combination unit. The image processor is embodied to execute a method according to the disclosure for generating combined image data.

For this purpose, the image processor typically has a processor comprising the registration unit and the combination unit. The image processor can be provided with the first MR data and/or the second MR data and/or a registration algorithm and/or a combination algorithm and/or a reconstruction algorithm and/or a trained function via the input. Further functions, algorithms or parameters required in the method can be provided to the image processor via the input. The combined image data and/or further results of an embodiment of the method according to the disclosure can be provided via the output. The registration unit is typically embodied to register the first MR data and the second MR data to one another and to generate first registered MR data and second registered MR data. The combination unit is typically embodied to statistically combine the first registered MR data and the second registered MR data. The image processor can be integrated in the image processing system. The image processor can also be installed separately from the image processing system. The image processor can be connected to the image processing system.

Embodiments of the image processing system according to the disclosure are embodied similarly to the embodiments of the method according to the disclosure. The image processing system can have further control components which are necessary and/or advantageous for executing a method according to the disclosure. Computer programs and further software by means of which the processor of the image processor automatically controls and/or executes a method sequence of a method according to the disclosure can be stored on a storage unit of the image processor.

A computer program product according to the disclosure can be loaded directly into a storage unit of a programmable image processor and has program code means for executing a method according to the disclosure when the computer program product is executed in the image processor, in particular in the processor of the image processing system according to the disclosure. This enables the method according to the disclosure to be executed quickly, identically repeatedly and robustly. The computer program product is configured such that it can execute the method steps according to the disclosure by means of the image processor. Herein, the image processor must in each case fulfil the requisite conditions such as, for example, having an appropriate random access memory, an appropriate graphics card or an appropriate logic unit so that the respective method steps can be executed efficiently. The computer program product is, for example, held on an electronically readable medium or on a network or server from where it can be loaded into the processor of a local image processor which is directly connected to the image processing system or can be embodied as part of the image processing system. Furthermore, control information of the computer program product can be stored on an electronically readable data carrier. The control information of the electronically readable data carrier can be embodied to perform a method according to the disclosure when the data carrier is used in an image processor of an image processing system. Examples of electronically readable data carriers are a DVD, a magnetic tape or a USB stick on which electronically readable control information, in particular software, is stored. When this control information (software) is read from the data carrier and stored in an image processor and/or processor of an image processing system, all the embodiments according to the disclosure of the above-described methods can be performed.

Furthermore, the disclosure is based on an electronically readable data carrier on which a program is held which is embodied to execute a method for generating combined image data.

Furthermore, the disclosure is based on a magnetic resonance device comprising a controller and an image processing system according to the disclosure. Hence, the magnetic resonance device is embodied to execute a method according to the disclosure for generating combined image data.

For this purpose, the controller typically has an input, a processor and an output. The controller can be provided with an MR control sequence, in particular an MR control sequence comprising the first sequence module, via the input. Further functions, algorithms or parameters required in the method can be provided to the controller via the input. The first MR data and/or the second MR data and/or further MR data and/or further results can be provided via the output. In an exemplary embodiment, the output of the controller is connected to the input of the image processor. The controller can be connected to the image processor. The image processor can be integrated in the controller. The controller and/or the image processing system can be integrated in the magnetic resonance device. The controller and/or the image processing system can also be installed separately from the magnetic resonance device. The controller and/or the image processing system can be connected to the magnetic resonance device.

The magnetic resonance device is embodied to acquire MR data, in particular first MR data and second MR data, from an examination area of an examination object, in particular by actuation by an MR control sequence. The controller is embodied to actuate individual components of the magnetic resonance device by playing out an MR control sequence, in particular an MR control sequence, comprising a first sequence module. Consequently, the magnetic resonance device according to the disclosure is embodied to execute an embodiment of the method according to the disclosure, said embodiment providing that the provision of the first MR data and the second MR data comprises recording the first MR data and the second MR data from the examination area of the examination object by actuating the magnetic resonance device according to an MR control sequence comprising the first sequence module. In an exemplary embodiment, the MR control sequence comprises the first sequence module at least twice at least partially offset in time. The MR control sequence may comprises a series of multiple sequence modules.

Embodiments of the magnetic resonance device according to the disclosure are embodied similarly to the embodiments of the method according to the disclosure. The magnetic resonance device can have further control components which are necessary and/or advantageous for executing a method according to the disclosure. The magnetic resonance device can also be embodied to send control signals and/or receive and/or to process control signals in order to execute a method according to the disclosure. In an exemplary embodiment, the image processor is part of the controller of the magnetic resonance device according to the disclosure. Computer programs and further software by means of which the processor of the image processor automatically controls or executes a process sequence of a method according to the disclosure can be stored on a storage unit of the image processor.

The advantages of the image processing system according to the disclosure, of the magnetic resonance device according to the disclosure, the computer program product according to the disclosure and the electronically readable data carrier according to the disclosure substantially correspond to the advantages of the method according to the disclosure for generating combined image data which are explained in detail above. Features, advantages or alternative embodiments can likewise be transferred to the other claimed subject matter and vice versa.

Figure 1:
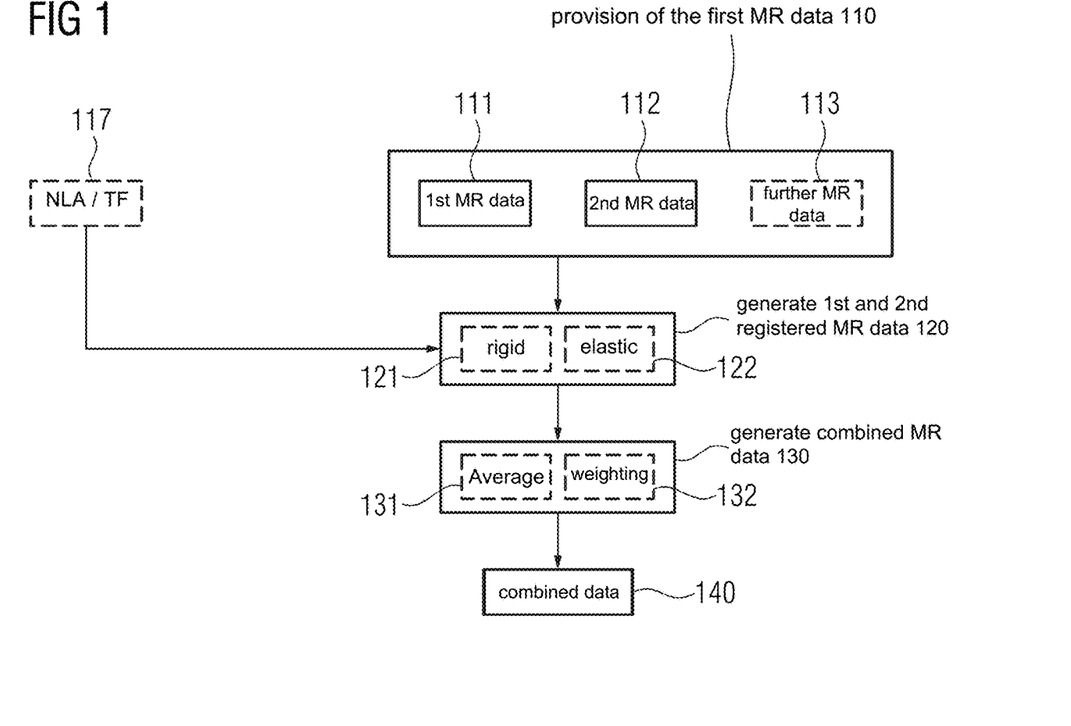
FIG. 1 a flowchart of a method according to an exemplary embodiment of the present disclosure.

FIG. 1 shows a flow diagram of a first embodiment of a method according to the disclosure. The method starts with method step 110, the provision of MR data. This method step 110 comprises method step 111, the provision of the first MR data, and method step 112, the provision of the second MR data, wherein the first and second MR data have each been generated from an examination area of an examination object by the actuation of the magnetic resonance device 16 using the first sequence module M1. Method step 110 can comprise, with method step 113, the provision of further MR data, said further MR data having been generated from the examination area of the examination object by the actuation of the magnetic resonance device 16 using the first sequence module M1. Method step 120 comprises the generation of first registered MR data and second registered MR data. Method step 130 provides the generation of combined image data by statistical combination of the first registered MR data and the second registered MR data. Method step 140 comprises the provision of the combined image data.

Method step 120 can comprise, with method step 121, a rigid registration and/or, with method step 122, an elastic registration. Optionally, the method can comprise method step 117, the provision of a non-linear algorithm and/or a trained function which is taken into account in the registration of the first MR data and the second MR data to one another in method step 120. Method step 130 can, in particular with method step 131, comprise averaging the first and second intensity values for each voxel. In addition or alternatively, with method step 132, the statistical combination is subject to weighting corresponding to a quality of the first registered MR data and the second registered MR data.

Figure 2:
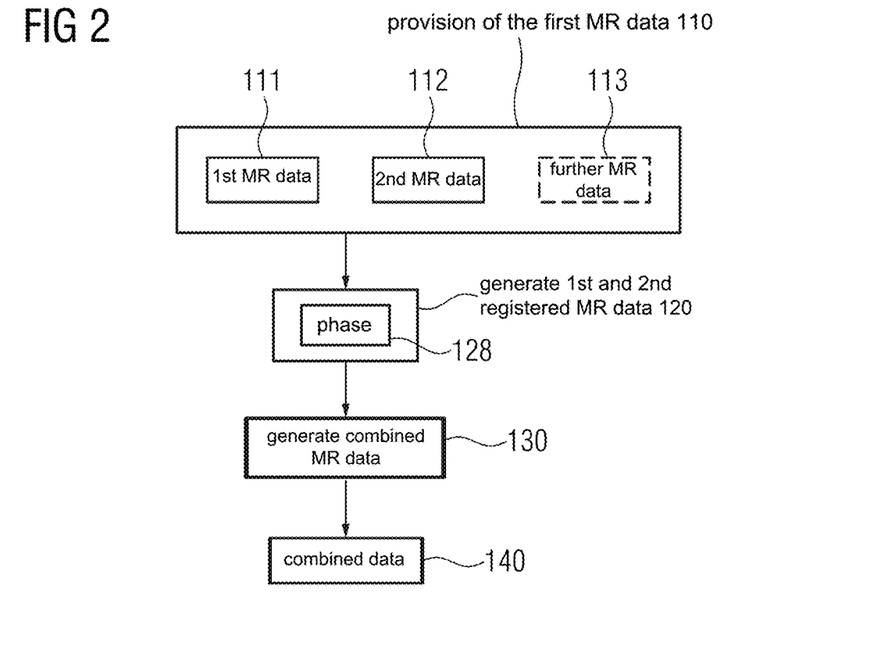
FIG. 2 a flowchart of a method according to an exemplary embodiment of the present disclosure.

FIG. 2 shows a flow diagram of a second embodiment of a method according to the disclosure. The second embodiment differs from the basic embodiment shown in FIG. 1 in method step 120 which, in the second embodiment with method step 128, comprises a registration taking into account a change in phase between the first raw data and the second raw data when the first MR data comprises first raw data and the second MR data comprises second raw data. Method step 128 can in particular be part of a rigid registration according to method step 121.

Figure 3:
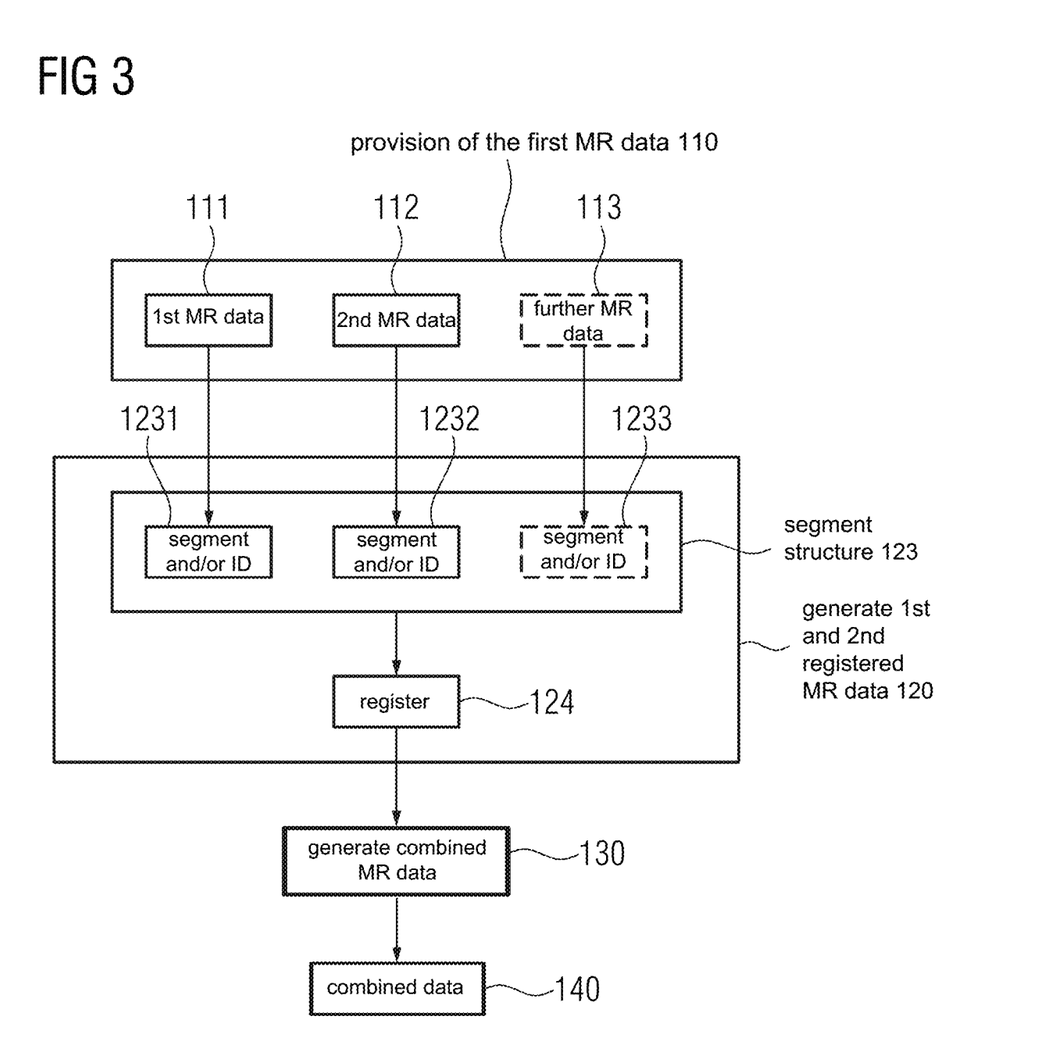
FIG. 3 a flowchart of a method according to an exemplary embodiment of the present disclosure.

FIG. 3 shows a flow diagram of a third embodiment of a method according to the disclosure. The third embodiment differs from the basic embodiment shown in FIG. 1 in method step 120 which, in the third embodiment with method step 123, comprises segmenting a structure comprised by the examination area and/or identifying a landmark comprised by the examination area for all MR data separately. The segmentation of a structure and/or identification of a landmark in the first MR data takes place in method step 1231, the segmentation of a structure and/or identification of a landmark in the second MR data takes place in method step 1232. If further MR data was provided in method step 110, 113, segmentation of a structure and/or identification of a landmark in the further MR data takes place in method step 1233. In addition, according to this embodiment, method step 120 comprises, with method step 124, registering the structure and/or the landmark of the MR data to one another.

Figure 4:
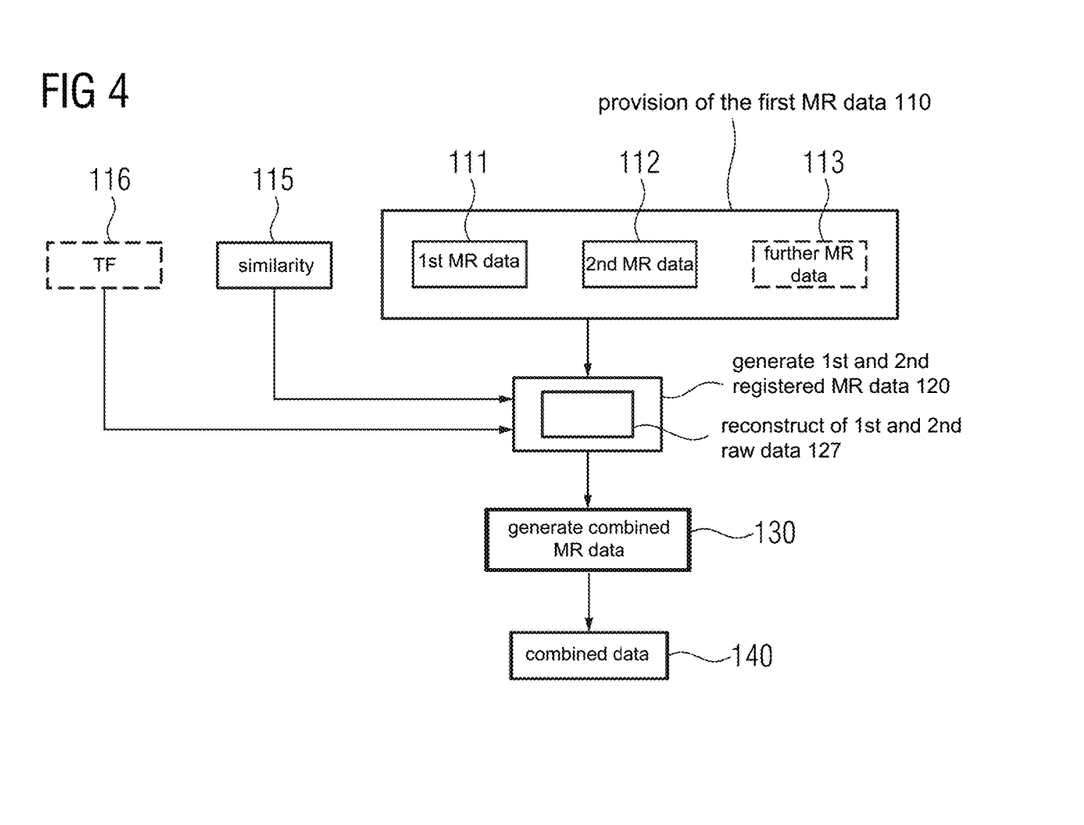
FIG. 4 a flowchart of a method according to an exemplary embodiment of the present disclosure.

FIG. 4 shows a flow diagram of a fourth embodiment of a method according to the disclosure. The fourth embodiment differs from the basic embodiment shown in FIG. 1 in method step 120 which, in the fourth embodiment with method step 127, comprises a reconstruction of the first raw data and the second raw data taking into account a similarity condition provided in method step 115 if the first MR data comprises first raw data and the second MR data comprises second raw data. Optionally, the reconstruction of the first raw data and the second raw data in method step 120 can take place using a trained function provided in method step 116.

Figure 5:
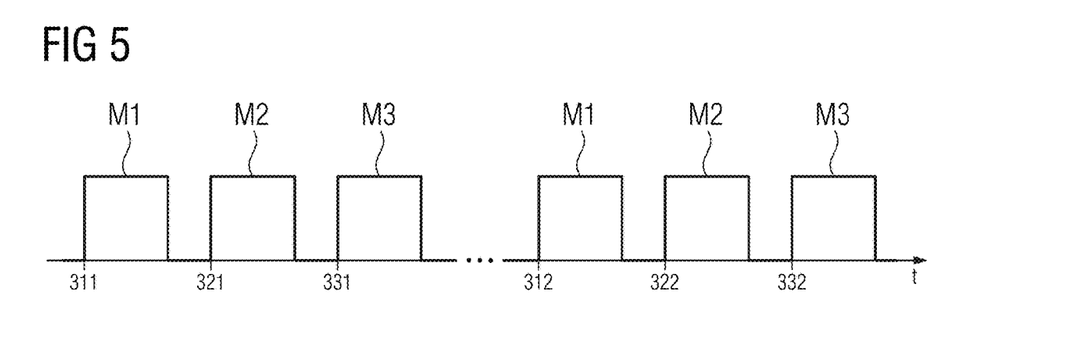
FIG. 5 a plot of a MR control sequence including a first sequence module according to an exemplary embodiment of the present disclosure.

FIG. 5 shows a plot of a MR control sequence in a schematic depiction. The time axis t is depicted horizontally. The MR control sequence comprises a first sequence module M1 at least twice, which is provided for generating first MR data from an examination area at a primary first time point 311 and for generating second MR data from the examination area at a secondary first time point 312.

In addition, the MR control sequence can comprise a second sequence module M2 and a third sequence module M3, which are provided for generating further first MR data in each case from a different further examination area different from one another at a primary further time point 321, 331 and for generating further second MR data from the in each case further examination areas that are different from one another at secondary further time points 322, 332. The temporal sequence of the sequence module M1, M2, M3 is shown by way of example. It is also conceivable for the time points 311, 312, 321, 322, 331, 332 to have another temporal sequence. In particular, the temporal sequence of the time points can, for example, be defined by the series 311, 312, 321, 322, 331, 332.

Between the primary first time point 311 and the secondary first time point 312, the examination object can have executed a movement and/or a change in position. In an exemplary embodiment, the primary first time point 311 and the secondary first time point 312 have a time difference of less than 10 minutes. In an exemplary embodiment, the sequence modules M1, M2, M3 comprise at least one radio-frequency excitation pulse, a radio-frequency refocusing pulse and a readout module, wherein the MR data of the corresponding examination area is read out. In an exemplary embodiment, such sequence modules M1, M2, M3 are part of an MR control sequence embodied as TSE or HASTE.

Figure 6:
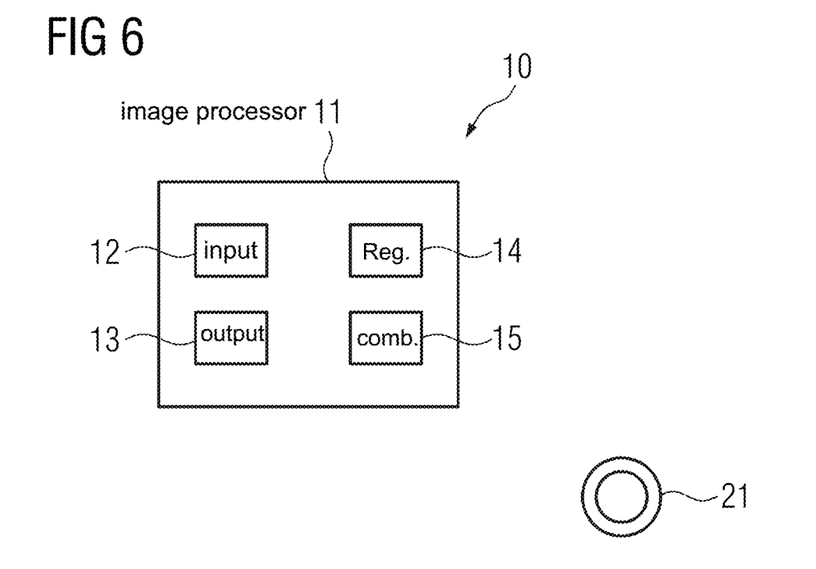
FIG. 6 an image processing system according to an exemplary embodiment of the present disclosure.

FIG. 6 shows an image processing system according to the disclosure 10 for executing a method according to the disclosure in a schematic depiction. The image processing system 10 comprises an image processor 11 with an input 12, an output 13, a registration unit (register/registrator) 14 and a combination unit (combiner) 15. The image processor 11 is also configured to execute a method for generating combined image data. For this purpose, the image processor 11 has computer programs and/or software, which can be loaded directly into a storage unit (memory) (not shown in further detail) of the image processor 11, with program means for executing a method for generating combined image data when the computer programs and/or software are executed in the image processor 11. For this purpose, the image processor 11 has a processor (not shown in further detail), which is configured to execute the computer programs and/or software. Alternatively thereto, the computer programs and/or software can also be stored on an electronically readable data carrier 21 embodied separately from the image processor 11, wherein data access from the image processor 11 to the electronically readable data carrier 21 can take place via a data network. The image processing system 10 depicted can obviously comprise usual further components of image processing systems 10. A method for generating combined image data can also be present in the form of a computer program product that implements the method on the image processor 11 when it is executed on the image processor 11. Likewise, an electronically readable data carrier 21 can be present with electronically readable control information stored thereupon, which comprises at least one such computer program product as described above and embodied such that it performs the described method when the electronically readable data carrier 21 is used in an image processor 11 of an image processing system 10. In an exemplary embodiment, the image processor 11 includes processing circuitry that is configured to perform one or more functions and/or operations of the image processor 11, including controlling the MR device 16, processing magnetic resonance signals, reconstructing magnetic resonance images, processing input from a user and/or providing an output to the user.

Figure 7:
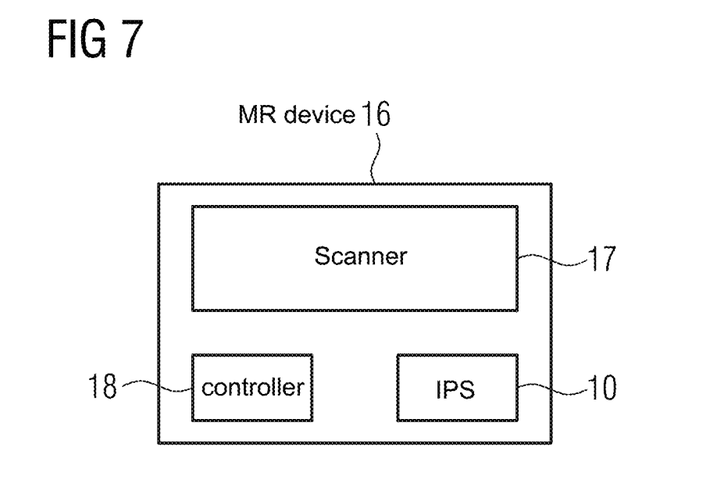
FIG. 7 a magnetic resonance device according to an exemplary embodiment of the present disclosure.

FIG. 7 shows a magnetic resonance device according to the disclosure 16 in a schematic depiction. The magnetic resonance (MR) device 16 comprises a scanner 17. The scanner 17 typically comprises (not shown in further detail)
- a main magnet for generating a strong and in particular constant main magnetic field,
- a patient receiving area for receiving an examination object,
- a gradient pulse unit used for spatial encoding during imaging, and
- a radio-frequency antenna unit for exciting polarization. To control the scanner 17, the magnetic resonance device 16 has a controller 18. The controller 18 controls the magnetic resonance device 16 centrally, such as, for example, the performance of MR control sequences. The magnetic resonance device 16 depicted can obviously comprise usual further components of magnetic resonance devices 16. Moreover, the general mode of operation of a magnetic resonance device 16 is known to the person skilled in the art so that no more detailed description of the further components will be given. The magnetic resonance device 16 comprises an image processing system according to the disclosure 10. Hence, together with the image processing system 10, the magnetic resonance device 16 is configured to execute a method according to the disclosure. In an exemplary embodiment, the image processor 11 includes processing circuitry that is configured to perform one or more functions and/or operations of the image processor 11 and/or one or more of the components of the image processor 11 includes processing circuitry that is configured to perform one or more functions and/or operations of the respective components.

Although the disclosure has been illustrated and described in greater detail by the preferred exemplary embodiments the disclosure is not restricted by the examples disclosed and other variations can be derived herefrom by the person skilled in the art without departing from the scope of protection of the disclosure.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein. In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

The invention claimed is:

1. A method for generating artifact-compensated combined image data based on first magnetic resonance (MR) data and second MR data, the method comprising:
providing the first MR data and the second MR data, the first MR data having been generated by a first actuation of a magnetic resonance device from an examination area of an examination object using a sequence module, and the second MR data having been generated by a second actuation of the magnetic resonance device from the examination area of the examination object using the sequence module;
registering the first MR data and the second MR data to one another to generate first registered MR data and second registered MR data;
statistically combining the first registered MR data and the second registered MR data on a voxel-by-voxel basis to generate combined image data that comprises a value for each voxel of the examination area to compensate for motion artifacts present in the first MR data and/or the second MR data as a result of changes to the examination area that occur between the first actuation and the second actuation; and
providing the combined image data in electronic form as a data file,
wherein the first MR data comprises first raw data and the second MR data comprises second raw data, and
wherein the registering is performed in the raw data space and is based on a change in phase between the first raw data and the second raw data.

2. The method as claimed in claim 1, wherein the examination area comprises a structure including a prostate, an abdomen, a pelvis, a chest, a head, a joint, and/or a musculoskeletal unit.

3. The method as claimed in claim 1, wherein the registering comprises a rigid registration.

4. The method as claimed in claim 1, wherein the registering comprises an elastic registration.

5. The method as claimed in claim 1, wherein the registering of the first MR data and the second MR data to one another comprises:
segmenting a structure comprised by the examination area and/or identifying a landmark comprised by the examination area in the first MR data and the second MR data; and
registering the structure and/or the landmark of the first MR data and the second MR data to one another.

6. The method as claimed in claim 1, wherein the first MR data comprises first raw data and the second MR data comprises second raw data, and
wherein the registering the first MR data and the second MR data to one another comprises a reconstruction of the first raw data and the second raw data based on a similarity condition.

7. The method as claimed in claim 6, wherein the reconstruction of the first MR data and the second MR data uses a trained function.

8. The method as claimed in claim 6, wherein:
the similarity condition comprises a threshold phase difference between the first raw data and the second raw data,
registering the first MR data and the second MR data comprises performing, when the threshold phase difference is exceeded, a phase correction of the first raw data and/or the second raw data, and
reconstruction of the first raw data and the second raw data comprises reconstruction of the phase corrected first raw data and/or the phase corrected second raw data.

9. The method as claimed in claim 1, wherein the registering the first MR data and the second MR data to one another uses a non-linear algorithm and/or a trained function.

10. The method as claimed in claim 1, wherein:
the first registered MR data comprises first image data having a first intensity value for each voxel comprised by the examination area,
the second registered MR data comprises second image data having a second intensity value for each voxel comprised by the examination area, and
the statistical combining of the first registered MR data and the second registered MR data comprises averaging the first and second intensity values for each voxel.

11. The method as claimed in claim 1, wherein the statistical combination of the first registered MR data and the second registered MR data comprises weighting corresponding to a quality of the first registered MR data and the second registered MR data.

12. The method as claimed in claim 11, wherein the weighting is a location-dependent weighting.

13. The method as claimed in claim 12, wherein the location-dependent weighting comprises an allocation of a quality-based weighting factor to locations within the first registered MR data and the second registered MR data such that locations with motion artifacts within the first registered MR data and/or the second registered MR data contribute less to the combined image data than locations without motion artifacts.

14. The method as claimed in claim 1, wherein the examination object has executed a movement and/or a change in position during one or more of the first actuation, the second actuation, between the first actuation, and between the second actuation.

15. The method as claimed in claim 1, wherein the first actuation and the second actuation have a time difference of less than 10 minutes.

16. The method as claimed in claim 1, wherein:
the sequence module is part of a same MR control sequence that includes at least two further sequence modules for generating further MR data from at least two further examination areas of the examination object,
the at least two further sequence modules are the same sequence modules, and
the at least two further examination areas are the same examination areas.

17. The method as claimed in claim 1, wherein the sequence module is part of a MR control sequence that includes a turbo spin-echo sequence (TSE) and/or a half-Fourier acquisition single-shot turbo spin-echo sequence (HASTE).

18. A non-transitory computer-readable storage medium with an executable program stored thereon that, when executed, instructs a processor to perform the method of claim 1.

19. The method as claimed in claim 1, wherein the first actuation and the second actuation at least partially overlap in time.

20. The method as claimed in claim 1, wherein the registering of the first MR data and the second MR data to one another is performed concurrently with at least a portion of a reconstruction of the first raw data and the second raw data, and
wherein the reconstruction of the first raw data and the second raw data is based upon the registration of the first MR data and the second MR data to one another.

21. An image processor comprising:
an input interface configured to provide first MR data and second MR data, the first MR data having been generated by a first actuation of a magnetic resonance device from an examination area of an examination object using a sequence module, and the second MR data having been generated by a second actuation of the magnetic resonance device from the examination area of the examination object using the sequence module;
a registrator configured to register the first MR data and the second MR data to one another to generate first registered MR data and second registered MR data;
a combiner configured to statistically combine the first registered MR data and the second registered MR data on a voxel-by-voxel basis to generate combined image data that comprises a value for each voxel of the examination area to compensate for motion artifacts present in the first MR data and/or the second MR data as a result of changes to the examination area that occur between the first actuation and the second actuation; and
an output interface configured to provide the combined image data in electronic form as a data file,
wherein the first MR data comprises first raw data and the second MR data comprises second raw data, and
wherein the registering is performed in the raw data space and is based on a change in phase between the first raw data and the second raw data.

22. A magnetic resonance (MR) device comprising:
an image processor; and
a controller configured to control the image processor to:
provide first MR data and second MR data, the first MR data having been generated by a first actuation of a magnetic resonance device from an examination area of an examination object using a sequence module, and the second MR data having been generated by a second actuation of the magnetic resonance device from the examination area of the examination object using the sequence module;
register the first MR data and the second MR data to one another to generate first registered MR data and second registered MR data;
statistically combine the first registered MR data and the second registered MR data on a voxel-by-voxel basis to generate combined image data that comprises a value for each voxel of the examination area to compensate for motion artifacts present in the first MR data and/or the second MR data as a result of changes to the examination area that occur between the first actuation and the second actuation; and
provide the combined image data in electronic form as a data file,
wherein the first MR data comprises first raw data and the second MR data comprises second raw data, and
wherein the registering is performed in the raw data space and is based on a change in phase between the first raw data and the second raw data.

* * * * *